US00PP18034P2

(12) United States Plant Patent
Dümmen

(10) Patent No.: US PP18,034 P2
(45) Date of Patent: Sep. 18, 2007

(54) ***GERANIUM* PLANT NAMED 'DUEAMANDA'**

(50) Latin Name: *Pelargonium×hortorum*
Varietal Denomination: Dueamanda

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 11/349,719

(22) Filed: Feb. 7, 2006

(51) Int. Cl.
*A01H 5/00* (2006.01)

(52) U.S. Cl. ..... Plt./327

(58) Field of Classification Search ..... Plt./325, Plt./327
See application file for complete search history.

(56) References Cited

U.S. PATENT DOCUMENTS

PP10,471 P * 6/1998 Lemon ..... Plt./325

OTHER PUBLICATIONS

UPOV ROM GTITM Computer Databast, GTI Jouve Retrieval Software 2006/05 Citation for 'Dueamanda'.*

* cited by examiner

*Primary Examiner*—Wendy Haas
(74) *Attorney, Agent, or Firm*—C. A. Whealy

(57) ABSTRACT

A new and distinct cultivar of Zonal *Geranium* plant named 'Dueamanda', characterized by its upright, somewhat outwardly spreading and rounded plant habit; freely branching habit; freely and early flowering habit; and salmon pink-colored double flowers.

1 Drawing Sheet

Botanical denomination: *Pelargonium×hortorum.*
Cultivar designation: 'Dueamanda'.

BACKGROUND OF THE INVENTION

The present invention relates to a new and distinct cultivar of Zonal *Geranium* plant, botanically known as *Pelargonium×hortorum,* and hereinafter referred to by the name 'Dueamanda'.

The new Zonal *Geranium* is a product of a planned breeding program conducted by the Inventor in Rheinberg, Germany. The objective of the breeding program was to develop new freely and early flowering Zonal *Geraniums* with attractive flower and foliage colors.

The new Zonal *Geranium* originated from a cross-pollination made by the Inventor on Jul. 1, 1998, of a proprietary selection of *Pelargonium×hortorum* identified as code number F-16-05, not patented, as the female, or seed, parent with a proprietary selection of *Pelargonium×hortorum* identified as code number F-19-05, not patented, as the male, or pollen, parent. The cultivar Dueamanda was discovered and selected by the Inventor as a flowering plant within the progeny from this cross-pollination in a controlled environment in Rheinberg, Germany on Jun. 1, 2004.

Asexual reproduction of the new cultivar by terminal vegetative cuttings at Rheinberg, Germany since Jul. 1, 2004, has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Dueamanda'. These characteristics in combination distinguish 'Dueamanda' as a new cultivar and distinguish it from other known Zonal *Geranium* cultivars:

1. Upright, outwardly spreading and rounded plant habit.
2. Freely branching habit.
3. Freely and early flowering habit.
4. Salmon pink-colored double flowers.

Compared to plants of the parent selections, plants of the new Zonal *Geranium* have darker-green color leaves. In addition, plants of the new Zonal *Geranium* and the parent selections differ in flower color as plants of the female parent selection have purple-colored flowers and plants of the male parent selection have orange-colored flowers.

The new Zonal *Geranium* can be compared to plants of the cultivar Miranda, not patented. In side-by-side comparisons conducted in Rheinberg, Germany, plants of the new Zonal *Geranium* differed from plants of the cultivar Miranda in the following characteristics:

1. Plants of the new Zonal *Geranium* had larger petals than plants of the cultivar Miranda.
2. Plants of the new Zonal *Geranium* had lighter salmon pink-colored petals than plants of the cultivar Miranda.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a typical flowering plant of 'Dueamanda' grown in a container.

DETAILED BOTANICAL DESCRIPTION

The cultivar Dueamanda has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5-cm containers. Plants were pinched once about three weeks after planting. Plants were about eight weeks from unrooted cuttings when the photograph and the detailed botanical description were taken. In the following description, color references are made to The Royal Horticultural Society Colour Chart, 1995 edition, except where general terms of ordinary dictionary significance are used.

Botanical classification: *Pelargonium×hortorum* cultivar Dueamanda.

Parentage:

*Female parent.*—Proprietary selection of *Pelargonium×hortorum* identified as F-16-05, not patented.

*Male parent.*—Proprietary selection of *Pelargonium×hortorum* identified as F-19-05, not patented.

Propagation:

*Type cutting.*—Terminal vegetative cuttings.

*Time to initiate roots, summer.*—About 5 days at 20° C.

*Time to initiate roots, winter.*—About 7 days at 20° C.

*Time to develop roots, summer.*—About three weeks at 20° C.

*Time to develop roots, winter.*—About four weeks at 20° C.

*Root description.*—Fine, fibrous; white in color.

*Rooting habit.*—Freely branching.

*Plant description.*—

*General appearance.*—Upright, somewhat outwardly spreading and rounded plant habit; densely foliated.

*Growth and branching habit.*—Moderately vigorous. Freely branching, about three to four lateral branches per plant.

*Plant height.*—About 23 cm.

*Plant width.*—About 21 cm.

*Lateral branches.*—Length: About 7 cm. Internode length: About 1.2 cm. Texture: Smooth, glabrous. Color: 144A.

*Foliage description.*—Arrangement: Alternate, simple. Length: About 5.7 cm. Width: About 7 cm. Shape: Reniform. Apex: Rounded. Base: Cordate. Margin: Crenate. Venation pattern: Palmate. Texture: upper and lower surfaces: Smooth, glabrous. Color: Developing and fully expanded foliage, upper surface: 137A; venation, 144A. Developing and fully expanded foliage, lower surface: 138A; venation, 144A. Zonation pattern: Distinct; in the center of the lamina. Width: About 1.5 cm. Color: 147A. Petiole: Length: About 5.5 cm. Diameter: About 2 mm. Texture, upper and lower surfaces: Smooth. Color, upper and lower surfaces: 144A.

Flower description:

*Flower arrangement.*—Salmon pink-colored double flowers arranged in rounded hemispherical umbels arising from apical leaf axils. Umbels displayed above and beyond the foliage on peduncles. Flowers rounded in form. Umbels persistent, flowers not persistent. Flowers not fragrant.

*Quantity of flowers.*—Freely flowering; at full flower, plants have about six flower umbels with about 25 to 30 flowers per umbel.

*Flower season.*—Flowering continuous spring through the summer. Plants begin flowering about eight weeks after planting.

*Flowering longevity.*—Flowers last about five to seven days on the plant.

*Umbel size.*—Diameter: About 10.75 cm. Height: About 6.3 cm.

*Flower size.*—Diameter: About 4.4 cm. Depth (height): About 1.8 cm.

*Flower buds.*—Length: About 1.4 cm. Diameter: About 8 mm. Shape: Ovoid. Color: 144A.

*Petals.*—Quantity per flower: About five. Length: About 2.7 cm. Width: About 2.1 cm. Shape: Obovate. Apex: Rounded. Base: Attenuate. Margin: Entire; sinuate. Texture, upper and lower surfaces: Smooth. Color: When opening and fully opened, upper surface: 41C; towards the apex, 49A; color does not fade with development. When opening and fully opened, lower surface: 41D; towards the apex, 49A.

*Petaloids.*—Quantity per flower: About two to four. Length: About 2.4 cm. Width: About 1.7 cm. Shape: Obovate. Apex: Rounded. Base: Attenuate. Margin: Entire; sinuate. Texture, upper and lower surfaces: Smooth. Color: When opening and fully opened, upper surface: 41C; towards the apex, 49A; color does not fade with development. When opening and fully opened, lower surface: 41D; towards the apex, 49A.

*Sepals.*—Quantity per flower: About five arranged in a single whorl. Length: About 9.4 mm. Width: About 2.3 mm. Shape: Elongated, tapering. Apex: Apiculate. Margin: Entire. Texture, upper and lower surfaces: Smooth; glabrous. Color, upper and lower surfaces: 144A.

*Peduncle* (*umbel stem*).—Length: About 12.5 cm. Diameter: About 1.5 cm. Angle: Mostly erect. Strength: Moderately strong. Texture: Smooth; glabrous. Color: 144A overlain with 178A.

*Pedicel* (*individual flower stem*).—Length: About 3.2 cm. Diameter: About 1 mm. Angle: Mostly erect. Strength: Moderately strong. Texture: Pubescent. Color: 59B.

*Reproductive organs.*—Androecium: Anther quantity per flower: About ten. Anther length: About 2 mm. Anther shape: Ovate. Anther color: 47C. Pollen amount: Moderate. Pollen color: 28A. Gynoecium: Pistil quantity per flower: One. Pistil length: About 1 cm. Stigma shape: Five-parted, star-shaped. Stigma color: 41A to 41B. Style length: About 5 mm. Style color: 41D. Ovary color: Close to 144A.

*Seed/fruit.*—Development of seeds and fruit have not been observed.

Disease/pest resistance: Plants of the new Zonal *Geranium* have not been observed to be resistant to pathogens and pests common to Zonal *Geraniums*.

Temperature tolerance: Plants of the new Zonal *Geranium* have been observed to be tolerant to temperatures ranging from about 5° C. to about 40° C.

It is claimed:

1. A new and distinct cultivar of Zonal *Geranium* plant named 'Dueamanda', as herein illustrated and described.

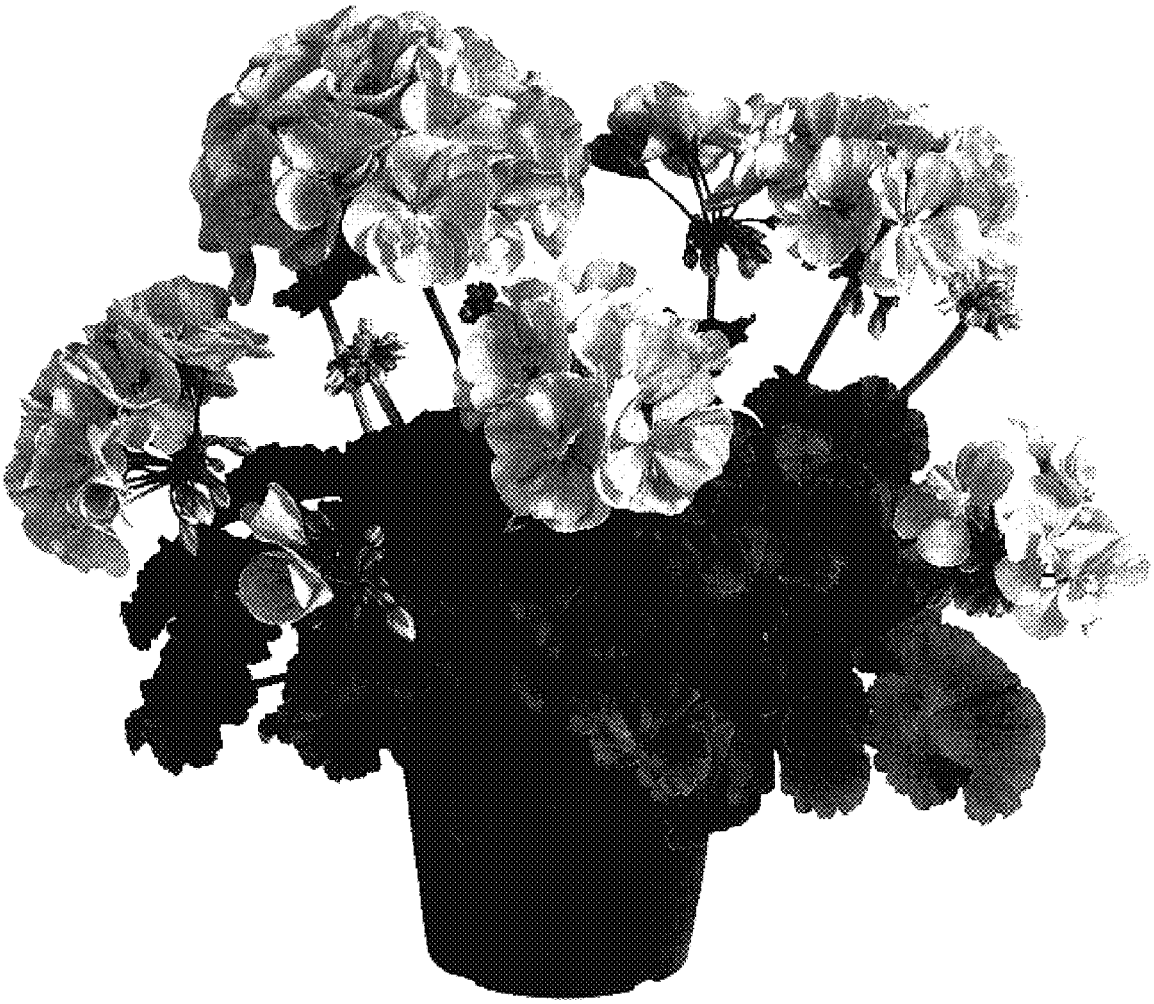

* * * * *